United States Patent
Weisgerber et al.

(10) Patent No.: US 6,284,246 B1
(45) Date of Patent: Sep. 4, 2001

(54) MODIFIED POLYPEPTIDES WITH HIGH ACTIVITY AND REDUCED ALLERGENICITY

(75) Inventors: David J. Weisgerber; Donn N. Rubingh, both of Cincinnati, OH (US)

(73) Assignee: The Procter & Gamble Co., Cincinnati, OH (US)

(*) Notice: Subject to any disclaimer, the term of this patent is extended or adjusted under 35 U.S.C. 154(b) by 0 days.

(21) Appl. No.: 08/903,298

(22) Filed: Jul. 30, 1997

(51) Int. Cl.$^7$ ................... A61K 6/00; A61K 7/00; A61K 38/43
(52) U.S. Cl. ........................... 424/94.1; 424/401
(58) Field of Search ............. 435/180; 424/49, 424/94.6, 400, 94.1, 401, 402; 514/844, 944, 947, 847

(56) References Cited

U.S. PATENT DOCUMENTS

| | | | |
|---|---|---|---|
| 4,179,337 | * 12/1979 | Davis et al. | 435/181 |
| 4,248,786 | 2/1981 | Batz | 260/326 |
| 4,556,554 | 12/1985 | Calvo | 424/70 |
| 4,670,417 | 6/1987 | Iwasaki | 514/6 |
| 4,760,025 | 7/1988 | Estell | 435/222 |
| 4,980,288 | 12/1990 | Bryan | 435/222 |
| 5,030,378 | 7/1991 | Venegas | 252/174 |
| 5,122,614 | 6/1992 | Zalipsky | 548/520 |
| 5,133,968 | 7/1992 | Nakayama | 424/401 |
| 5,230,891 | * 7/1993 | Nakayama et al. | 424/401 |
| 5,446,090 | 8/1995 | Harris | 525/54 |
| 5,643,575 | 7/1997 | Martinez et al. | 424/94.1 |
| 5,707,848 | 1/1998 | Bryan et al. | 435/222 |
| 5,856,451 | * 1/1999 | Olsen et al. | 530/402 |
| 6,159,688 | 12/2000 | Borchert et al. | 435/6 |

FOREIGN PATENT DOCUMENTS

| | | | |
|---|---|---|---|
| 0251446 B1 | 1/1988 | (EP) | C12N/15/00 |
| 0407225 A1 | 1/1991 | (EP) | C12N/15/55 |
| 0516200 A1 | 12/1992 | (EP) | C11D/3/386 |
| WO 91/06637 | 5/1991 | (WO) | C12N/9/48 |
| WO 92/10755 | 6/1992 | (WO) | G01N/33/53 |
| WO 93/15189 | 8/1993 | (WO) | C12N/9/96 |
| WO 93/19731 | 10/1993 | (WO) | A61K/7/48 |
| WO 93/19732 | 10/1993 | (WO) | A61K/7/48 |
| WO 95/10615 | 4/1995 | (WO) | C12N/15/57 |
| WO 95/29979 | 11/1995 | (WO) | C11D/3/386 |
| WO 95/30010 | 11/1995 | (WO) | C12N/15/57 |
| WO 95/30011 | 11/1995 | (WO) | C12N/15/57 |
| WO 96/17929 | 6/1996 | (WO) | C12N/9/96 |
| WO 96/21469 | 7/1996 | (WO) | A61K/47/48 |
| WO 96/28475 | 9/1996 | (WO) | C07K/17/08 |
| WO 96/40791 | 12/1996 | (WO) | C07K/17/08 |

OTHER PUBLICATIONS

Abuchowski, A. et al. "Cancer Therapy with Chemically Modified Enzymes. I. Anti–tumor Properties of Polyethylene Glycol–Asparaginase Conjugates", *Cancer Biochem Biophys*, vol. 7, (1984) pp. 175–186.

Caliceti, P. et al., "Active Site Protection of Proteolytic Enzymes by Poly(ethylene glycol) Surface Modification" *Journal of Bioactive and Compatible Polymers*, vol. 8—Jan., 1993, pp. 41–50.

Delgado, C. et al. "The Uses and Properties of PEG–Linked Proteins", *Critical Review in Therapeutic Drug Carrier systems*, 9(3,4) (1992) pp. 249–304.

Francis, G. E. et al., "PEG–Modified Proteins", *Stability of Protein Pharmaceuticals, Part B: In Vivo Pathways of Degradation and Strategies for Protein Stabilization*, edited by Ahern, T. J. and Mannin, M.C., Plenum Press (1992) pp. 235–263.

Katre, N. V. "The Conjugation of Proteins with Polyethylene Glycol and Other Polymers" *Advanced Drug Delivery Reviews*, 10 (1993) pp. 91–114.

Khan, S. A. et al., "Polyethylene Glycol–modified Subtilisin Forms Microparticulate Suspensions in Organic Solvents", *Enzyme Microb. Technology*, vol. 14, Feb. (1992), pp. 96–100.

Monfardini, C. et al., "A branched monoethoxy poly(ethylen glycol) for Protein Modification", Bioconjugate Chemistry, vol. 6, No. 1 (1995), pp. 62–69.

Nishimura, H. et al., "Improved Modification of Yeast Uricase with Polyethylene Glycol, Accompanied with Non-immunoreactivity towards Anti–Uricase Serum and High Enzymic Activity", *Enzyme* 26 (1981): pp. 49–53.

(List continued on next page.)

*Primary Examiner*—Thurman K. Page
*Assistant Examiner*—S. Howard
(74) *Attorney, Agent, or Firm*—Stephen T. Murphy; Dara M. Kendall; Fumiko Tsuneki

(57) ABSTRACT

The present invention relates to a modified polypeptide which has an enzymatic activity level of greater than about 70% of the parent polypeptide and an allergenic response level of less than about 33% of the parent polypeptide. Embodiments of the present invention relate to modified polypeptides with reduced allergenicity and high enzymatice activity comprising the formula:

$$A\text{-}B_n$$

wherein A is an enzyme, and mixtures thereof; B is a twin polymer moiety, having a total molecular weight of from about 0.5 kilodaltons (KD) to about 40 KD, having the formula

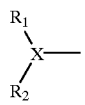

conjugated to the enzyme; wherein $R_1$ and $R_2$ are essentially straight chain polymers, having a molecular weight ranging from about 0.25 KD to about 20 KD; wherein the ratio of the molecular weights of $R_1$ and $R_2$ is from about 1:10 to about 10:1; wherein X is a linking moiety which links the twin moeity to a single site on the enzyme; and n is the number of twin polymer moietis conjugated to the enzyme, and represents an integer from about 1 to about 15.

22 Claims, No Drawings

OTHER PUBLICATIONS

Nucci, M. L. et al. "Immunogencity of Polyethylene Glycol–Modified Superoxide Dismutase and Catalase", *Journal of Free Radicals in Biology & Medicine*, vol. 2, pp 321–325 (1986).

Nucci, M. L. et al., "The Therapeutic Value of Poly(ethylene glycol)–modified Proteins" *Advanced Drug Delivery Reviews*, 6 (1991) pp. 133–149.

Savoca, K. V. et al., "Preparation of a Non–Immunogenic Agrinase by the Covalent Attachment of Polyethylene Glycol", *Biochemica et Biophysica Acta*, 578 (1979) pp. 47–53.

Zalipsky, S. et al., "A Convenient general method for synthesis of $N^{\alpha}$– or $N^{\omega}$– dithiasuccinoyl (Dts) amino acids and dipeptides: application of polyethylene glycol as a carrier for functional purification", *International Journal of Peptide Protein Research*, 30, (1987) pp. 740–783.

Masunaga, T. et al., "The Protease as a Cleansing Agent and Its Stabilization by Chemical Modification", IFSCC, Yokohama pp. 483–501.

Masakatsu Ohta, et. al., "Preparation of a Dextran–Protease Conjugate and its Application to Cosmetic Use", Kanebo, Ltd., Cosmetics Laboratory, Japan pp. 727–743.

Abuchowski. A., et. al., "Soluble Polymer–Enzyme Adducts", Rutgers University, New Brunswick, NJ pp. 367–383.

Lee, V., "Peptide and Protein Drug Delivery", University of California School of Pharmacy, Los Angeles, CA. pp. 831–857.

Inada, Y., et al., "Biomedical and Biotechnological Applications of PEG– and PM–modified Proteins", TIBTECH, vol. 13, pp. 86–90 (Mar. 1995).

Veronese, F. M., et al., "Improvement of Pharmacokinetic, Immunological and Stability Properties of Asparaginase by Conjugation to Linear and Branched Monomethoxy poly ethylene glycol", Journal of Controlled Release, vol. 40, pp. 199–209 (1996).

* cited by examiner

MODIFIED POLYPEPTIDES WITH HIGH ACTIVITY AND REDUCED ALLERGENICITY

TECHNICAL FIELD

The present invention relates to modified polypeptides, specifically lipase and protease enzymes, with high activity and reduced allergenicity.

BACKGROUND OF THE INVENTION

An increasing number of commercial products containing active polypeptides are becoming available. The majority of these products utilize an enzyme as the polypeptide. Enzymes are polypeptides which react with a compound, or substrate, to break down that compound. Enzymes are divided into numerous classes based on the class of substrate they react upon. Each class of enzyme generally catalyzes the severing of different chemical bonds resulting in the specific selection of activity. The lipase class of enzymes are known for their ability to hydrolyze ester bonds created between, but not limited to, hydrocarbons and polyalcohol backbone substrates. Examples of these substrates are mono-, di-, and triglyceride—polyglycerol esters. The protease class of enzymes are known for their ability to hydrolyze proteins. Naturally occurring and bio-engineered protease enzymes are incorporated into household cleaning detergents to hydrolyze proteinaceous dirt and stains, into personal care products to remove dirt and dead skin, into oral cleansing products to facilitate plaque removal in the mouth, and medicines to affect undesired proteins in the body.

It is known that current commercial cleansing products are made more effective by the incorporation of protease polypeptides. U.S. Pat. No. 4,261,868 (Hora et al.), U.S. Pat. No. 4,404,115 (Tai), U.S. Pat. No. 4,318,818 (Letton et al.), European Patent Application 130,756 (published Jan. 9, 1985) and U.S. Pat. No. 5,030,378 (Venegas) all disclose the use of protease polypeptides in cleansing or detergent products.

It is also realized, however, that polypeptides are potential antigens, and may cause allergic reactions in humans, under certain conditions. The human immune system can produce specific antibodies upon exposure to polypeptides. This process of producing specific antibodies is referred to as "immunization" when a clinically beneficial response is obtained. When the response leads to hypersensitivity, however, it is referred to as "sensitization". Allergenic sensitization to polypeptides has been observed in environments where humans are regularly exposed to the polypeptide. Such environments include manufacturing facilities, where workers can be exposed to uncontrolled dust or aerosol containing a polypeptide, or the marketplace, where consumers' repeated use of products containing polypeptides has, on occasion, caused an allergic reaction.

Presently, allergic responses to polypeptides can be minimized by immobilizing, granulating, coating or dissolving the polypeptides to avoid their becoming airborne. These methods, while addressing consumer exposure to airborne polypeptides, still leave the risks associated with extended tissue contact with the finished product and exposure to enzyme-containing dust or aerosol during manufacturing.

Another way of diminishing allergic response has been to select polypeptides of human origin. While this approach minimizes allergenicity problems, it is not a complete solution since it is often not possible to find such a polypeptide which also has the activity properties desired.

A third proposition for decreasing allergenicity has been to reduce the size of the polypeptide molecules (see JP Patent Publication Number 4,112,753). However, size reduction can cause a significant reduction in enzyme activity.

A fourth approach to reduce the allergenicity of polypeptides is through epitope mapping and alteration of the polypeptide amino acid sequence to deliver a polypeptide with reduced allergenicity. This approach usually requires a large investment of development time and money.

In the medical field, suggestions have been made to diminish the immunogenicity of polypeptides through yet another method. This method involves attaching unreactive polymers to the polypeptide. U.S. Pat. No. 4,179,337 (Davis, et al.) relates to polypeptides coupled to substantially straight chain polyethylene glycol (PEG) or polypropylene glycol (PPG) polymer moieties. While PEG/PPG coupling was found to mitigate the allergenicity of the polypeptide, only 15% of the physiological activity was maintained. PCT Application WO 96/17929 (Olsen, et al., published Jun. 13, 1996) relates to the modification of polypeptides by conjugating them with suitable polymers. The Olsen application describes modified polypeptides which demonstrate a reduction in allergenicity of from 25% to 66% compared to the parent polypeptide, while maintaining from 39% to 100% of the activity of the parent.

Monfardini, et al, "A Branched Monomethoxypoly (ethylene glycol) for Protein Modification", American Chemical Society, 1995) describes efforts to increase the activity of native polypeptides by conjugating branched monomethoxypolyethylene glycol (mPEG) polymers to the reactive enzyme group. Monfardini, et al. teaches conjugation of enzymes with linear mPEG polymers having molecular weight 5000 KD and branched mPEG polymers having a molecular weight of 5000 KD per branch. Conjugation to ribonuclease, catalase, trypsin and asparaginase is shown. Enzymatic activity levels of conjugated enzyme are shown to range from 86% to 133% of the activity of the respective parent enzyme. No allergenicity data is presented.

It would be highly desirable to develop an enzyme-based compound which would virtually eliminate allergenic responses while maintaining the desired high levels of enzymatic activity. If this were accomplished it would provide manufacturers and consumers with safer ways to utilize the benefits of enzyme technology.

It is an object of the present invention to provide a modified enzyme compound which delivers this high activity and yet shows reduced stimulation of and resulting activation of the immune system. It is also an object to provide compositions of use of this modified enzyme compound.

SUMMARY OF THE INVENTION

The present invention relates to a modified polypeptide which has an enzymatic activity level of greater than about 70% of the parent polypeptide and an allergenic response level of less than about 33% of the parent polypeptide. Embodiments of the present invention relate to modified polypeptides with reduced allergenicity and high enzymatic activity comprising the formula:

$$A\text{-}B_n$$

wherein A is an enzyme selected from the group consisting of lipase enzymes and protease enzymes, and mixtures thereof; B is a twin polymer moiety, having a total molecular weight of from about 0.5 kilodaltons (KD) to about 40 KD, having the formula

conjugated to the enzyme; wherein $R_1$ and $R_2$ are essentially straight chain polymers, having a molecular weight ranging from about 0.25 KD to about 20 KD; wherein the ratio of the molecular weights of $R_1$ and $R_2$ is from about 1:10 to about 10:1; wherein X is a linking moiety which links the twin moiety to a single site on the enzyme; and n is the number of twin polymer moieties conjugated to the enzyme, and represents an integer from about 1 to about 15.

DETAILED DESCRIPTION OF THE INVENTION

The modified polypeptide of the present invention is represented by the formula:

$$A\text{-}B_n$$

containing, as essential components, a enzyme, A, and a plurality, n, of twin polymer moieties, B. While not intending to be limited by theory, it is believed that the conjugation of the twin polymer moieties to the enzyme provides a balanced stearic hindrance of the activated surface of the enzyme as to allow for high activity but simultaneously prevent stimulation of the immune system and subsequent antibody formation responsible for allergic reaction.

As used herein, the phrase "amino acid sequence" refers to a specific configuration of the amino acids comprising a polypeptide. The following is a list of abbreviations used herein to describe amino acids:

| Amino Acid | Three-letter Abbreviation | One-letter Symbol |
|---|---|---|
| Alanine | Ala | A |
| Arginine | Arg | R |
| Asparagine | Asn | N |
| Aspartic Acid | Asp | D |
| Cysteine | Cys | C |
| Glutamine | Gln | Q |
| Glutamic Acid | Glu | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| No amino acid at position | Xaa | * |

As used herein, the term "mutation" refers to the genetic alteration of an organism, which in turn alters the amino acid sequence of the enzyme produced by that organism. The mutation of an enzyme has been often found to alter the properties of the enzyme.

As used herein, the term "wild-type" refers to an enzyme produced by unmutated hosts.

As used herein, the term "variant", means an enzyme having an amino acid sequence which differs from that of the wild-type enzyme due to the genetic mutation of the host producing that enzyme.

As used herein, the term "parent polypeptide" is defined as the enzyme, wild-type or variant, with no additional conjugation of polymer moieties. The activity and allergenicity of the parent polypeptide are usually well known from their development and use in medical and/or consumer products.

The essential components of the present invention, as well as a non-exclusive list of preferred and optional ingredients, are described in detail below.

ENZYME

An essential component of the present invention is an active enzyme. Any enzyme can be used in the modified polypeptide herein. Preferred enzymes are selected from the group consisting of protease enzymes and lipase enzymes. Mixtures of proteases and lipases are also included.

Lipase enzymes are classified under the Enzyme Classification number E.C. 3.1.1 (Carboxylic Ester Hydrolases) in accordance with the Recommendations (1992) of the International Union of Biochemistry and Molecular Biology (IUBMB). Examples of lipases include lipases derived from the following microorganisms. The indicated patent publications are incorporated herein by reference:

Humicola, (U.S. Pat. No. 4,810,414)

Pseudonomas (WO 89/04361, U.S. Pat. No. 4,950,417, EP 218 272, WO 88/09367, U.S. Pat. No. 5,389,536)

Fusarium (EP 130 064, WO 90/09446)

Mucor (EP 238 023)

Chromobacterium

Aspergillus

Candida (WO 88/02775, WO 94/01541, WO 89/02916)

Geotricum

Penicillium

Rhizopus

Bacillus (WO 91/16422)

Specific examples of commercial lipases include Lipolase®, Lipolase™ Ultra, Lipozyme®, Palatase®, Novozym435, Lecitase® (all available from Novo Nordisk A/S); Lumafast™ and Lipomax (available from Genencor Int., Inc.).

Protease enzymes are classified under the Enzyme Classification number E.C. 3.4 (Carboxylic Ester Hydrolases) in accordance with the Recommendations (1992) of the International Union of Biochemistry and Molecular Biology (IUBMB). Useful proteases are also described in PCT publications: WO 95/30010 published Nov. 9, 1995 by The Procter & Gamble Company; WO 95/30011 published Nov. 9, 1995 by The Procter & Gamble Company; WO 95/29979 published Nov. 9, 1995 by The Procter & Gamble Company.

Preferred protease enzymes for use in the modified polypeptides herein are subtilisin, chymotrypsin and elastase-type protease enzymes.

Especially preferred for use herein are subtilisin-type protease enzymes. Subtilisin enzymes are naturally produced by *Bacillus alcalophilus, Bacillus amyloliquefaciens, Bacillus amylosaccharicus, Bacillus licheniformis, Bacillus lentus* and *Bacillus subtilis* microorganisms.

A particularly preferred substilisin-type enzyme is bacterial serine protease enzyme, and variants thereof, obtained from *Bacillus amyloliquefaciens, Bacillus licheniformis* and/or *Bacillus subtilis*, including Novo Industries A/S Alcalase®, Esperase®, Savinase® (Copenhagen, Denmark), Gist-brocades' Maxatase®, Maxacal® and Maxapem 15® (protein engineered Maxacal®) (Delft, Netherlands), and subtilisin BPN and BPN', which are commercially available.

Especially preferred are protease enzymes, and variants thereof, obtained from *Bacillus amyloliquefaciens*. One known enzyme is is BPN'. The wild-type BPN' from *Bacillus amyloliquefaciens* is characterized by the amino acid sequence:

```
  1                                          10
Ala Gln Ser Val Pro Tyr Gly Val Ser Gln

20
Ile Lys Ala Pro Ala Leu His Ser Gln Gly

30
Tyr Thr Gly Ser Asn Val Lys Val Ala Val

40
Ile Asp Ser Gly Ile Asp Ser Ser His Pro

50
Asp Leu Lys Val Ala Gly Gly Ala Ser Met

60
Val Pro Ser Glu Thr Asn Pro Phe Gln Asp

70
Asn Asn Ser His Gly Thr His Val Ala Gly

80
Thr Val Ala Ala Leu Asn Asn Ser Ile Gly

90
Val Leu Gly Val Ala Pro Ser Ala Ser Leu

100
Tyr Ala Val Lys Val Leu Gly Ala Asp Gly

110
Ser Gly Gln Tyr Ser Trp Ile Ile Asn Gly

120
Ile Glu Trp Ala Ile Ala Asn Asn Met Asp

130
Val Ile Asn Met Ser Leu Gly Gly Pro Ser

140
Gly Ser Ala Ala Leu Lys Ala Ala Val Asp

150
Lys Ala Val Ala Ser Gly Val Val Val Val

160
Ala Ala Ala Gly Asn Glu Gly Thr Ser Gly

170
Ser Ser Ser Thr Val Gly Tyr Pro Gly Lys

180
Tyr Pro Ser Val Ile Ala Val Gly Ala Val

190
Asp Ser Ser Asn Gln Arg Ala Ser Phe Ser

200
Ser Val Gly Pro Glu Leu Asp Val Met Ala

210
Pro Gly Vai Ser Ile Gln Ser Thr Leu Pro

220
Gly Asn Lys Tyr Gly Ala Tyr Asn Gly Thr

230
Ser Met Ala Ser Pro His Val Ala Gly Ala

240
Ala Ala Leu Ile Leu Ser Lys Ris Pro Asn

250
Trp Thr Asn Thr Gln Val Arg Ser Ser Leu

260
Glu Asn Thr Thr Thr Lys Leu Gly Asp Ser

270
Phe Tyr Tyr Gly Lys Lys Gly Leu Ile Asn

175
Asn Val Gln Ala Ala Ala Gln
```

Variants of BPN', hereafter referred to as "Protease A", are disclosed in U.S. Pat. No. 5,030,378 (issued to Venegas, Jul. 9, 1991) as characterized by the BPN' amino acid sequence with the following mutations:

a.) the Gly at position Gly166 is replaced with Asn, Ser, Lys, Arg, His, Gin, Ala or Glu; the Gly at position Gly169 is replaced with Ser; the Met at position Met222 is replaced with Gln, Phe, Cys, His, Asn, Glu, Ala or Thr; or b.) the Gly at position Gly166 is replaced with Lys and the Met at position Met222 is replaced with Cys; or c.) the Gly at position Gly160 is replaced with Ala and the Met at position Met222 is replaced with Ala.

Additional variants of BPN', heretoforth referred to as "Protease B", are disclosed by Genencor International, Inc. (San Francisco, Calif.) European Patent EP-B-251,446 (granted Dec. 28, 1994 and published Jan. 7, 1988) as characterized by the wild-type BPN' amino acid with the mutations in one or more of the following amino acids: Tyr21, Thr22, Ser24, Asp36, Ala 45, Ala48, Ser49, Met50, His67, Ser87, Lys94, Val95, Gly97, Ser101, Gly102, Gly103, Ile107, Gly110, Met 124, Gly127, Gly128, Pro129, Leu135, Lys170, Tyr171, Pro172, Asp197, Met 199, Ser 204, Lys213, Tyr214, Gly215, and Ser221; or two or more of the amino acids listed above and Asp32, Ser33, Tyr104, Ala152, Asn155, Glu156, Gly166, Gly169, Phe189, Tyr217, and Met222 wherein both mutations cannot be made on the Asp32, Ser33, Tyr104, Ala152, Asn155, Glu156, Gly166, Gly169, Phe189, Tyr217, and Met222 amino acids.

Another preferred BPN' variant protease, hereafter referred to as "Protease D", is described in WO 95/10615 published Apr. 20, 1995 by Genencor International as characterized by the wild-type BPN' amino acid with mutation to position Asn76, in combination with mutations in one or more other amino acid positions selected from the group consisting of Asp99, Ser101, Gln103, Tyr104, Ser105, Ile107, Asn109, Asn123, Leu126, Gly127, Gly128, Leu135, Glu156, Gly166, Glu195, Asp197, Ser204, Gln206, Pro210, Ala216, Tyr217, Asn218, Met222, Ser260, Lys265, and/or Ala274.

Another preferred BPN' variant protease, hereafter referred to as "Protease F", is described in U.S. Pat. No. 4,760,025, issued to Estell, et al. on Jul. 26, 1988 as characterized by the wild-type BPN' amino acid with mutation to one or more amino acid positions selected from the group consisting of Asp32, Ser33, His64, Tyr104, Asn155, Glu156, Gly166, Gly169, Phe189, Tyr217, and Met222.

Preferred proteolytic enzymes, then, are selected from the group consisting of Alcalase®, BPN', Protease A, Protease B, Protease D, and Protease F, and mixtures thereof. Protease F is most preferred.

TWIN POLYMER MOIETIES

The enzyme employed in the present invention is modified by conjugation of a plurality, n, of twin polymer moieties to the enzyme, wherein n is the average number of moieties conjugated to a polypeptide. The average number of moieties per polypeptide can range from about 1 to about 15, preferably from about 2 to about 10, and more preferably from about 3 to about 5.

The twin polymer moiety has a total molecular weight of from about 0.5 KD to about 40 KD, preferably from about 0.5 KD to about 20 KD, and more preferably from about 1.0 KD to about 10 KD.

The twin polymer moiety of the present invention has the following structure

wherein $R_1$ and $R_2$ are essentially straight chain polymers having a molecular weight of from about 0.5 kilodaltons (KD) to about 20 KD, preferably from about 1.0 KD to about 10 KD and more preferably from about 2 KD to about 5 KD, and X is a linking moiety which connects the twin polymer moiety to a single site on the enzyme. The ratio of the molecular weights of $R_1$ and $R_2$ can range from 1:10 to about 10:1, preferably from 1:5 to about 5:1 and more preferably from 1:3 to about 3:1.

Examples of the suitable polymers which comprise the twin polymer moiety include polyethylene glycols, methoxypolyethylene glycols, polypropylene glycols, polyvinyl alcohols, poly-carboxylates, poly-vinylpyrolidones, poly-D, L-amino acids, dextrans including carboxymethyldextrans, celluloses including methylcellulose, carboxymethylcellulose, ethylcellulose, hydroxyethyl cellulose, carboxyethyl cellulose and hydroxypropylcellulose, hydrolysates of chitosan, starches including hydroxyethyl-starches and hydroxypropyl-starches, glycogen, agaroses and derivatives thereof, guar gum, pullulan, inulin, xanthan gum, carrageenin, pectin, alginic acid hydrolysates and bio-polymers. Mixtures of polymers can also be used to form the twin polymer moiety. The preferred polymer is polyethylene glycol.

Suitable linking moieties can be taken from the class of materials capable of being functionalized appropriately to link two polymer chains, while maintaining functionality to reactive groups on desired peptide groups within the enzyme. Examples of linking moieties and related chemistry are disclosed in U.S. Pat. No. 5,446,090, Harris, issued Aug. 29, 1995; U.S. Pat. No. 5,171,264, Merrill, issued Dec. 15, 1992; U.S. Pat. No. 5,162,430, Rhee et al., issued Nov. 10, 1992; U.S. Pat. No. 5,153,265, Shadle et al., issued Oct. 6, 1992; and U.S. Pat. No. 5,122,614, Zalipsky, issued Jun. 16, 1992, all herein incorporated by reference.

Preferable examples of these linking moieties are:

a) Twin-polymer-succinimide to couple to Lysine, Tyrosine, Histidine, etc., where an amide or ester linkage is formed:

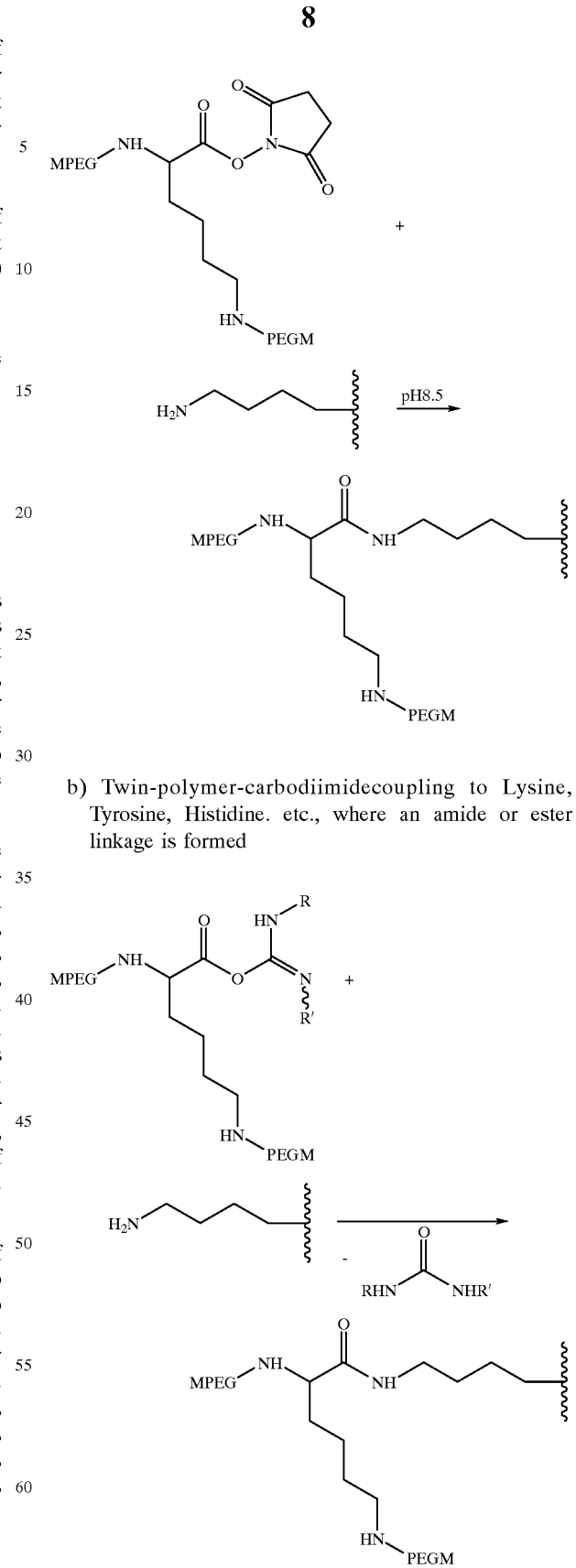

b) Twin-polymer-carbodiimidecoupling to Lysine, Tyrosine, Histidine. etc., where an amide or ester linkage is formed c) Twin-polymer-CH$_2$OH coupling to Glutamic or Aspartic acid forming an ester linkage

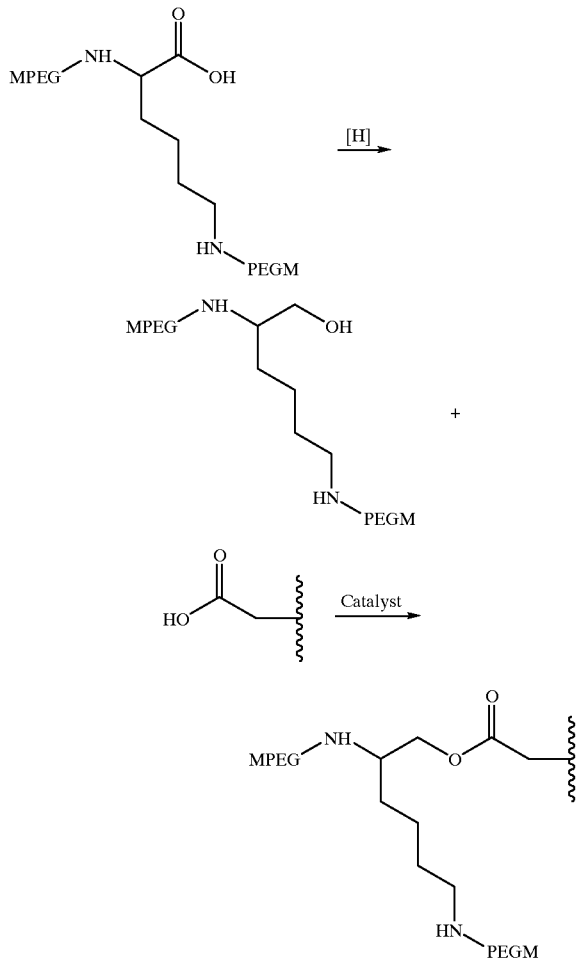

d) Twin-polymer-aldehyde coupling to Lysine forming an imine or amine linkage depending on whether reducing agent (e.g. NaCNBH$_3$) is used. The preferred linking moiety, X, is an activated lysine succinimidyl ester of the form

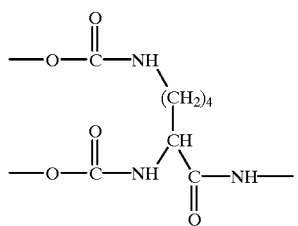

This activated lysine succinidyl ester reacts with the amino acid group of lysine, arginine and histidine peptides of the enzyme. Therefore, the most preferred structure of the twin polymer moiety of the present invention is

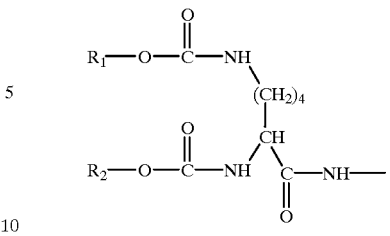

The polypeptide of the present invention can also comprise combinations of twin polymer moieties to achieve the activity and reduced allergenicity required.

ENZYMATIC ACTIVITY AND ALLERGENICITY

The modified polypeptides of the present invention provides both high enzymatic activity and significantly reduced allergenicity when compared to their respective parent polypeptides. The particular modified polypeptides of the present inventions have an enzymatic activity level of greater than about 70%, preferably greater than about 80%, and more preferably greater than about 90%, of the parent polypeptide as measure by the Enzymatic Activity Method set forth hereinafter in the Analytical Methods Section. Moreover, the particular modified polypeptides of the present inventions have an allergenic response level of less than about 33%, preferably less than about 20%, more preferably less than about 10% and most preferably less than about 5%, of the parent polypeptide as measure by the Allergenic Response Method set forth hereinafter in the Analytical Methods Section.

METHOD OF MANUFACTURE

In reaction vessel, add polypeptide, in solution of 0.2M Borate buffer at 8.5 pH. Add one-fourth of the activated twin-polymer, maintaining the reaction temperature at approximately 25 C. and let react 30 minutes. Repeat the addition of activated twin-polymer every 30 minutes over a 2 hour period. Buffer exchange through YM30 Amicon setup at 4° C. with 0.01M KH$_2$PO$_{4,\ 5.5}$ pH buffer. Remove excess reactants via filtration.

COMPOSITIONS OF USE

The modified polypeptides herein can be used in any application which is suitable for the respective parent polypeptide. The modified polypeptides are used at levels of greater than about 0.001%, preferably greater than about 0.01%, and most preferably greater than about 0.1% and at levels less than about 20%, preferably less than about 10%, and most preferably less than 5%.

For example the modified polypeptides herein can be incorporated into laundry compositions, hard surface cleansing products, light duty cleansing compositions, automatic dishwasher detergent compositions, leave-on and rinse-off hair conditioners, hair shampoos, leave-on and rinse-off facial acne preparations, facial milks and conditioners, shower gels, foaming and non-foaming facial cleansers, cosmetics, hand and body lotions, leave-on facial moisturizers, cosmetic and cleansing wipes, oral cleansing compositions and enzymatic contact lens cleansing solutions. These products are all manufactured using standard procedures using standard materials known in the respective arts.

Examples of each type of composition are shown in the references below, all herein incorporated by reference.

Personal cleansing compositions

Skin cleansers—U.S. Pat. No. 5,641,479, Linares et al, issued Jun. 24, 1997; U.S. Pat. No. 5,599,549, Wivell et al., issued Feb. 4, 1997; U.S. Pat. No. 5,585,104, Ha et al., issued Dec. 17, 1996; U.S. Pat. No. 5,540,852, Kefauver et al., issued Jul. 30, 1996; and U.S. Pat. No. 5,510,050, Dunbar et al., issued Apr. 23, 1996.

Facial acne preparations—U.S. Pat. No. 5,612,324, Guang Lin et al., issued Mar. 18, 1997; U.S. Pat. No. 5,587,176, Warren et al., issued Dec. 24, 1996; U.S. Pat. No. 5,549,888, Venkateswaran, issued Aug. 27, 1996; and U.S. Pat. No. 5,470,884, Corless et al., issued Nov. 28, 1995.

Shower gels—U.S. Pat. No. 5,650,384, Gordon et al., issued Jul. 22, 1997; and U.S. Pat. No. 5,607,678, Moore et al., issued Mar. 4, 1997.

Hair conditioners and shampoos—U.S. Pat. No. 5,624,666, Coffindaffer et al., issued Apr. 29, 1997; U.S. Pat. No. 5,618,524, Bolich, Jr. et al., issued Apr. 8, 1997; U.S. Pat. No. 5,612,301, Inman, issued Mar. 18, 1997; U.S. Pat. No. 5,573,709, Wells, issued Nov. 12, 1996; U.S. Pat. No. 5,482,703, Pings, issued Jan. 9, 1996; and U.S. Pat. No. Re. 34,584, Grote et al., Reissued Apr. 12, 1994.

Topical skin care compositions

Cosmetics—U.S. Pat. No. 5,641,493, Date et al., issued Jun. 24, 1997; U.S. Pat. No. 5,605,894, Blank et al., issued Feb. 25, 1997; U.S. Pat. No. 5,585,090, Yoshioka et al., issued Dec. 17, 1996.

Hand, face, and body lotions—U.S. Pat. No. 4,939,179, Cheney et al., issued Jul. 3, 1990; and U.S. Pat. No. 5,607,980, McAtee et al., issued Mar. 4, 1997.

Cosmetic and cleansing wipes—U.S. Pat. No. 4,045,364, Richter et al., issued Aug. 30, 1977; European Patent Application, EP 0 619 074, Touchet et al., published Oct. 12, 1994; and U.S. Pat. No. 4,975,217, Brown-Skrobot et al., issued Dec. 4, 1990

Laundry cleansing compositions

Liquidfabric detergents—U.S. Pat. No. 4,261,868, Hora et al., issued Apr. 14, 1981; U.S. Pat. No. 4,404,115, Tai, issued Sep. 13, 1983, U.S. Pat. No. 4,318,818, Letton et al., issued Mar. 9, 1982.

Granularfabric detergents—U.S. Pat. No. 5,569,645, Dinnewell et al., issued Oct. 29, 1996; U.S. Pat. No. 5,554,587, Scott, issued Sep. 10, 1996; U.S. Pat. No. 5,458,810, Fredj et al., issued Oct. 17, 1995; U.S. Pat. No. 4,379,080, Murphy, issued Apr. 5, 1983; U.S. Pat. No. 4,412,934, Chung et al., issued Nov. 1, 1983.

Other cleansing compositions

Oral cleaning compositions (including dentifrice compositions, mouthwashes, lozenges, chewing gum, and denture cleansing tablets)—U.S. Pat. No. 5,096,700, Seibel, issued Mar. 17, 1992; U.S. Pat. No. 5,028,414, Sampathkumar, issued Jul. 2, 1991 and U.S. Pat. No. 5,028,415, Benedict, et al., issued Jul. 2, 1991.

Enzymatice contact lens cleaning solution—U.S. Pat. No. 4,863,627, Davies, et al., Sep. 5, 1989; U.S. Pat. No. Re. 32,672, Huth, et al., reissued May 24, 1988; and U.S. Pat. No. 4,609,493, Schafer, issued Sep. 2, 1986.

Hard surface cleansing products—U.S. Pat. No. 4,943,392, Hastedt et al., issued Jul. 24, 1990.

Light duty dish cleansing compositions—U.S. Pat. No. 5,599,400, Mao et al., issued Feb. 4, 1997; U.S. Pat. No. 5,545,354, Ofosu-Asante, issued Aug. 13, 1996; and U.S. Pat. No. 5,635,466, Burdon et al., issued Jun. 3, 1997.

Automatic dishwasher detergent compositions—U.S. Pat. No. 5,616,277, Raleigh et al., issued Apr. 1, 1997; U.S. Pat. No. 5,614,485, Painter, issued Mar. 25, 1997; U.S. Pat. No. 5,578,136, Taylor et al., issued Nov. 26, 1996; and U.S. Pat. No. 5,559,089, Hartman et al., issued Sep. 24, 1996.

ANALYTICAL METHODS

ENZYMATIC ACTIVITY METHOD

The enzymatic activity of a polypeptide or a modified polypeptide is assayed by measuring the rate of reaction of the polypeptide or modified polypeptide with a substrate.

Substrates

For proteases: Enzymatic activity of proteases is measured using the substrate succiny-Ala-Ala-Pro-Pbep-Nitroaniline (PNA). Proteases cleave the bond between the peptide and p-nitroaniline to give a visible yellow color absorbing at 410 nm.

For lipases: Enzymatic activity of lipases is measured using the substrate p-nitrophenyl carbrilate. Lipases cleave the bond between the caprilate and the p-nitrophenyl to give a visible yellow color absorbing at 410 nm.

Equipment:

Any calibrated spectrophotometer with the capability to measure the rate of change of absorbance at 410 nm. can be used.

Materials:

Buffer Solution: 0.1M Tris (Tris Hydroxy Methyl Amino Methane), 0.01M $CaCl_2$, pH 8.6. (For example mix 21.7 g.Tris (Tris Hydroxy Methyl Amino Methane), 2.6 g. $CaCl_2$-$2H_2O$ and 1.8 L distilled deionized filtered $H_2O$).

Substrate Solution: 20 mg of the appropriate substrate is dissolved into 1ml dimethyl sulfoxide (DMSO).

Polypeptide Solutions: A solution of modified polypeptide and a solution of parent polypeptide having equal polypeptide concentrations as measured by spectrophotometric absorbance at 280 nm.

Working solution: 252.5 $\mu$l of substrate solution is diluted up to 25 ml with buffer solution.

Procedure:

1. Mix 10 $\mu$l of test polypeptide solution and 990 $\mu$l. buffer solution in flask.

2. In separate vessel add 50 $\mu$l of solution from step 1. to 950 $\mu$l buffer solution.

3. In spectrophotometer flask, add 990 $\mu$l of working solution.

4. Add 10 $\mu$l of solution from step 2 to spectrophotometer flask. Record the absorbance at 410 nm as a function of the time and ABS/min. The temperature should be controlled (20–25C. depending on the protease).

Data and Results

The Enzymatice Activity Level is the ratio of the slope of absorbance versus time (Abs/min) of the modified polypeptide to the slope of absorbance versus time of the parent polypeptide and multiplied by 100 to present the activity as a percent of the parent.

ALLERGENIC RESPONSE METHOD

The allergenic response of polypeptides is measured utilizing ELISA (Enzyme Linked Immunosorbant Assay) technique. Antibody binding is quantitated for both parent and modified polypeptide with the amount bound for the modified polypeptide, at equal polypeptide concentrations, expressed as a percentage of the amount bound to the parent.

Reductions in the percentage of antibody bound to the modified polypeptide is predictive of reduced in-vivo immune response.

Procedure:

1. A microtiter plate is coated with 100 μL/well rabbit anti-Enzyme-base antibody (2 μg/mL in 15 mM sodium carbonate, 35 mM sodium bicarbonate buffer, pH 9.6) overnight. Unbound coating antibody is washed out with wash buffer (0.5M NaCl, 13 mM Trizma-base, 0.2% BSA, 0.5% Tween 20, pH 8.0), then blocked one hour with 100 μL/well 2% BSA in water.
2. A series of Enzyme standards ranging from 0.2–20 ng/mL are prepared in sample prep buffer (6.6 mM Trizma-base, 0.5M NaCl, 1 mM $CaCl_2 \cdot 2H_2O$, 30 mM $Na_2S_2O_3$, 0.1% BSA, 0.1% Tween 20, pH 8.0).
3. For each modified Enzyme sample, the parent material (unmodified Enzyme) is required at the same concentration (by protein level) as a reference, as measured by spectrophotometry at 280 nm. The sample and its reference are then diluted equally into sample prep buffer to bring them into the range of the standard curve.
4. Standards, samples and references are added to the coated, blocked and washed plate at 50 μL/well. Sample prep buffer is used for the blank. Then 50 μL/well of a dilute solution of rabbit anti-Enzyme antibody, alkaline phosphatase conjugate in assay buffer (0.5M NaCl, 50 mM Trizma-base, 1.5% BSA, 0.15% Tween 20, pH 8.4) is added. The plate is incubated for 2 hrs. at 37° C., then emptied and washed.
5. P-nitrophenylphosphate substrate solution (1 mg/mL in diethanolamine buffer) is added to the wells at 100 μL/well. The plate is incubated at 37° C. until sufficient color has developed, about 30 minutes. Absorbances are read in a microtiter plate reader in the dual wavelength mode at 405 nm with reference wavelength of 620 nm.
6. The net absorbances of the standards are plotted against their concentrations to generate a standard curve. The concentrations of the samples and their references are calculated from the curve. The "percent antibody binding retained" is calculated by dividing the concentration of the sample by the concentration of its reference and multiplying by 100.

EXAMPLES

The following are nonlimiting examples of the modified polypeptides of the present invention.

Example 1

Protease B is conjugated with an average of three (n=3) twin polymer moieties consisting of two polyethylene glycol moieties, each with a molecular weight of 5000 KD and an activated lysine succinimidyl ester. The modified polypeptide is prepared by adding of 20 mg Protease B and 15 ml of 0.2M Borate, pH 8.5, buffer solution to a reaction vessel. The reaction temperature is maintained at approximately 25° C. Approximately 240 mg Twin PEG 10K Succinimide (Shearwater Polymers, Inc.) is added to the reaction vessel and reacted for 30 minutes. Three more additions 240 mg Twin PEG Succinimide is made every 30 minutes for a total added of 960 mg. of Twin PEG 10K Succinimide added over a 2 hour period. The solution buffers are exchanged with 0.01M $KH_2PO_4$, 5.5 pH buffer and filtered to remove excess reactants.

Example 2

Protease F is conjugated with an average of eight (n=8) twin polymer moieties consisting of two polyethylene glycol moieties, each with a molecular weight of 2000 KD and an activated lysine succinimidyl ester. The modified polypeptide is prepared by adding of 20 mg Protease F and 15 ml of 0.2M Borate, pH 8.5, buffer solution to a reaction vessel. The reaction temperature is maintained at approximately 25° C. Approximately 240 mg Twin PEG 4K Succinimide is added to the reaction vessel and reacted for 30 minutes. Three more additions 240 mg Twin PEG 4K Succinimide is made every 30 minutes for a total added of 960 mg. of Twin PEG 4K Succinimide added over a 2 hour period. The solution buffers are exchanged with 0.01M $KH_2PO_4$, 5.5 pH buffer and filtered to remove excess reactants.

Example 3

Protease F is conjugated with an average of five (n=5) twin polymer moieties consisting of two polyethylene glycol moieties, each with a molecular weight of 2000 KD and an activated lysine succinimidyl ester. The modified polypeptide is prepared by adding of 20 mg Protease F and 15 ml of 0.2M Borate, pH 8.5, buffer solution to a reaction vessel. The reaction temperature is maintained at approximately 25° C. Approximately 150 mg Twin PEG 4K Succinimide is added to the reaction vessel and reacted for 30 minutes. Three more additions 150 mg Twin PEG 4K Succinimide is made every 30 minutes for a total added of 600 mg. of Twin PEG 4K Succinimide added over a 2 hour period. The solution buffers are exchanged with 0.01M $KH_2PO_4$, 5.5 pH buffer and filtered to remove excess reactants.

Example 4

Protease A is conjugated with an average of five (n=5) twin polymer moieties consisting of two polyethylene glycol moieties, each with a molecular weight of 4000 KD and an activated carbodiimide. The modified polypeptide is prepared by adding of 20 mg Protease A and 15 ml of 0.2M Borate, pH 8.5, buffer solution to a reaction vessel. The reaction temperature is maintained at approximately 25° C. Approximately 300 mg Twin PEG 8K Carbodiimide is added to the reaction vessel and reacted for 30 minutes. Three more additions 300 mg Twin PEG Succinimide is made every 30 minutes for a total added of 1200 mg. of Twin PEG 8K Carbodiimide added over a 2 hour period. The solution buffers are exchanged with 0.01M $KH_2PO_4$, 5.5 pH buffer and filtered to remove excess reactants.

Example 5

Protease F is conjugated with an average of eight (n=8) twin polymer moieties consisting of two polyethylene glycol moieties, each with a molecular weight of 5000 KD and an activated carbodiimide. The modified polypeptide is prepared by adding of 20 mg Protease F and 15 ml of 0.2M Borate, pH 8.5, buffer solution to a reaction vessel. The reaction temperature is maintained at approximately 25° C. Approximately 640 mg Twin PEG 10K Carbodiimide is added to the reaction vessel and reacted for 30 minutes. Three more additions 640 mg Twin PEG Succinimide is made every 30 minutes for a total added of 2560 mg. of Twin PEG 8K Carbodiimide added over a 2 hour period. The solution buffers are exchanged with 0.01M $KH_2PO_4$, 5.5 pH buffer and filtered to remove excess reactants.

Example 6

Protease F is conjugated with an average of eight (n=8) twin polymer moieties consisting of two polyethylene glycol moieties, each with a molecular weight of 5000 KD and an activated lysine succinimidyl ester. The modified polypeptide is prepared by adding of 20 mg Protease F and 15 ml of 0.2M Borate, pH 8.5, buffer solution to a reaction vessel. The reaction temperature is maintained at approximately 25° C. Approximately 640 mg Twin PEG 10K Succinimide is added to the reaction vessel and reacted for 30 minutes. Three more additions 640 mg Twin PEG Succinimide is made every 30 minutes for a total added of 2560 mg. of Twin PEG 10K Succinimide added over a 2 hour period. The solution buffers are exchanged with 0.01M $KH_2PO_4$, 5.5 pH buffer and filtered to remove excess reactants.

Example 7

Protease B is conjugated with an average of three (n=3) twin polymer moieties consisting of two polyethylene glycol moieties, each with a molecular weight of 10,000 KD and an activated lysine succinimidyl ester. The modified polypeptide is prepared by adding of 20 mg Protease B and 15 ml of 0.2M Borate, pH 8.5, buffer solution to a reaction vessel. The reaction temperature is maintained at approximately 25° C. Approximately 480 mg Twin PEG 20K Succinimide is added to the reaction vessel and reacted for 30 minutes. Three more additions 480 mg Twin PEG 20K Succinimide is made every 30 minutes for a total added of 19200 mg. of Twin PEG 10K Succinimide added over a 2 hour period. The solution buffers are exchanged with 0.01M $KH_2PO_4$, 5.5 pH buffer and filtered to remove excess reactants.

Example 8

Protease A is conjugated with an average of three (n=3) twin polymer moieties consisting of two polyvinyl alcohol moieties, each with a molecular weight of 20,000 KD and an activated lysine succinimidyl ester. The modified polypeptide is prepared by adding of 20 mg Protease A and 15 ml of 0.2M Borate, pH 8.5, buffer solution to a reaction vessel. The reaction temperature is maintained at approximately 25° C. Approximately 960 mg Twin PVA 40K Succinimide is added to the reaction vessel and reacted for 30 minutes. Three more additions 960 mg Twin PVA Succinimide is made every 30 minutes for a total added of 3840 mg. of Twin PVA 40K Succinimide added over a 2 hour period. The solution buffers are exchanged with 0.01M $KH_2PO_4$, 5.5 pH buffer and filtered to remove excess reactants.

Example 9

Protease B is conjugated with an average of four (n=4) twin polymer moieties, where the moieties are a equal molar mixture of two polyethylene glycol moieties. One moiety has twin polyethylene glycol moieties, each with a molecular weight of 1000 KD and the other has twin polyethylene glycol moieties, each with a molecular weight of 5000 KD. Both contain an activated lysine succinimidyl ester linking agent. The modified polypeptide is prepared by adding of 20 mg Protease B and 15 ml of 0.2M Borate, pH 8.5, buffer solution to a reaction vessel. The reaction temperature is maintained at approximately 25° C. Approximately 320 mg of an equal molar mixture of Twin PEG 2K Succinimide and Twin PEG 10K Succinimide (both from Shearwater Polymers, Inc.) is added to the reaction vessel and reacted for 30 minutes. Three more additions of 320 mg of the Twin PEG mixture is made every 30 minutes for a total added of 1280 mg. of Twin PEG mixture added over a 2 hour period. The solution buffers are exchanged with 0.01M $KH_2PO_4$, 5.5 pH buffer and filtered to remove excess reactants.

The following examples further describe and demonstrate embodiments within the scope of the present invention. In the following examples, all ingredients are listed at an active level. The examples are given solely for the purpose of illustration and are not to be construed as limitations of the present invention, as many variations thereof are possible without departing from the spirit and scope of the invention.

Ingredients are identified by chemical or CTFA name.

Examples 10–13
Bodywash Products

|  | Ex. 10 | Ex. 11 | Ex. 12 | Ex. 13 |
|---|---|---|---|---|
|  | (Wgt %) | | | |
| Water | 55.00 | 55.00 | 55.00 | 55.00 |
| Disodium EDTA | 0.20 | 0.20 | 0.20 | 0.20 |
| Glycerine | 3.00 | 3.00 | 3.00 | 3.00 |
| Polyquaternium 1o | 0.40 | 0.40 | 0.40 | 0.40 |
| Sodium/Magnesium Laureth-3-3.6 Sulphate | 12.00 | 12.00 | 12.00 | 12.00 |
| Cocamide MEA | 2.80 | 2.80 | 2.80 | 2.80 |
| Sodium Lauraphoacetate | 6.00 | 6.00 | 6.00 | 6.00 |
| Myristic Acid | 1.60 | 1.60 | 1.60 | 1.60 |
| Magnesium Sulphate Hepta Hydrate | 0.30 | 0.30 | 0.30 | 0.30 |
| Trihydroxystearin | 0.50 | 0.50 | 0.50 | 0.50 |
| PEG-6 Caprylic/Capric Triglycerides | 3.00 | 0.00 | 0.00 | 0.00 |
| Sucrose Polyesters of Cottonate Fatty Acid | 3.00 | 0.00 | 0.00 | 0.00 |
| Sucrose Polyesters of Behenate Fatty Acid | 3.00 | 0.00 | 4.00 | 0.00 |
| Petrolatum | 0.00 | 4.00 | 8.00 | 0.00 |
| Mineral Oil | 0.00 | 0.00 | 0.00 | 6.00 |
| DMDM Hydantoin | 0.08 | 0.08 | 0.08 | 0.08 |
| Modified Polypeptides of Example 1–9 | 0.10 | 2.00 | 2.00 | 5.00 |
| Citric Acid | 1.40 | 1.40 | 1.40 | 1.40 |
| Water | q.s. | q.s. | q.s. | q.s |
|  | 100.00 | 100.00 | 100.00 | 100.00 |

Examples 14–17
Facewash Products

|  | Ex. 14 | Ex. 15 | Ex. 16 | Ex. 17 |
|---|---|---|---|---|
|  | (Wgt %) | | | |
| Water | 50.00 | 50.00 | 50.00 | 50.00 |
| Disodium EDTA | 0.10 | 0.10 | 0.20 | 0.20 |
| Citric Acid | 0.00 | 0.00 | 1.40 | 1.40 |
| Sodium Laureth-3 Sulfate | 3.00 | 3.50 | 0.00 | 0.00 |
| Sodium Laureth-4 Carboxylate | 3.00 | 3.50 | 0.00 | 0.00 |
| Laureth-12 | 1.00 | 1.20 | 0.00 | 0.00 |
| Polyquaternium 10 | 0.00 | 0.00 | 0.40 | 0.40 |
| Polyquaternium 25 | 0.30 | 0.30 | 0.00 | 0.00 |
| Glycerine | 3.00 | 3.00 | 3.00 | 3.00 |
| Sodium Lauroamphoacetate | 0.00 | 0.00 | 6.00 | 6.00 |
| Lauric Acid | 6.00 | 6.00 | 3.00 | 3.00 |
| Myristic Acid | 0.00 | 0.00 | 3.00 | 3.00 |
| Magnesium Sulphate Hepta Hydrate | 2.30 | 2.00 | 2.00 | 2.00 |
| Triethanol Amine | 4.00 | 4.00 | 4.00 | 4.00 |
| Trihydroxystearin | 0.50 | 0.50 | 0.50 | 0.50 |
| Sucrose Polyesters of Behenate Fatty Acid | 2.00 | 2.00 | 0.00 | 0.00 |
| Sucrose Polyesters of Cottonate Fatty Acid | 3.00 | 2.00 | 0.00 | 0.00 |
| PEG-6 Caprylic/Capric Triglycerides | 0.00 | 0.00 | 0.00 | 2.00 |
| Petrolatum | 0.00 | 0.00 | 4.00 | 0.00 |
| Mineral Oil | 0.00 | 0.00 | 0.00 | 2.00 |
| Cocamidopropyl Betaine | 2.00 | 3.00 | 1.80 | 1.80 |

-continued

|  | Ex. 14 | Ex. 15 | Ex. 16 | Ex. 17 |
|---|---|---|---|---|
|  | (Wgt %) | | | |
| Lauryl Dimethyl Amine Oxide | 1.00 | 1.20 | 1.20 | 1.20 |
| Dex Panthenol | 1.00 | 0.25 | 0.25 | 0.00 |
| DMDM Hydantoin | 0.08 | 0.08 | 0.08 | 0.08 |
| Modified Polypeptide of Examples 1–9 | 1.00 | 2.00 | 0.50 | 0.50 |
| Fragrance | 0.20 | 0.20 | 0.20 | 0.20 |
| Water | q.s. | q.s. | q.s. | q.s. |
|  | 100.00 | 100.00 | 100.00 | 100.00 |

Examples 18–19

Leave-on Skin Moisturizing Composition

|  | Ex. 18 | Ex. 19 |
|---|---|---|
|  | (Wgt %) | |
| Glycerine | 5.00 | 0.00 |
| Stearic Acid | 3.00 | 0.00 |
| C11–13 Isoparaffin | 2.00 | 0.00 |
| Glycol Stearate | 1.50 | 0.00 |
| Propylene Glycol | 0.00 | 3.00 |
| Mineral Oil | 1.00 | 10.00 |
| Sesame Oil | 0.00 | 7.00 |
| Petrolatum | 0.00 | 1.80 |
| Triethanolamine | 0.70 | 0.09 |
| Cetyl Acetate | 0.65 | 0.00 |
| Glyceryl Stearate | 0.48 | 2.00 |
| TEA Stearate | 0.00 | 2.50 |
| Cetyl Alcohol | 0.47 | 0.00 |
| Lanolin Alcohol | 0.00 | 1.80 |
| DEA-Cetyl Phosphate | 0.25 | 0.00 |
| Methylparaben | 0.20 | 0.20 |
| Propylparaben | 0.12 | 0.10 |
| Carbomer 934 | 0.11 | 0.00 |
| Disodium EDTA | 0.10 | 0.00 |
| Modified Polypeptide of Examples 1–9 | 0.10 | 0.5 |
| Water | q.s. | q.s |

Example 20

Cleansing Wipe Composition

| Cleansing composition | |
|---|---|
|  | (Wgt %) |
| Propylene Glycol | 1.00% |
| Ammonium Lauryl Sulfate | 0.60% |
| Succinic Acid | 4.00% |
| Sodium Succinate | 3.20% |
| Triclosan ® | 0.15% |
| Modified Polypeptide of Examples 1–9 | 0.05% |
| Water | q.s. to 100% |

The cleansing composition above is impregnated onto a woven absorbent sheet comprised cellulose and/or polyester at about 250% by weight of the absorbent sheet Examples 21–24

Shampoo

|  | Ex. 21 | Ex. 22 | Ex. 23 | Ex. 24 |
|---|---|---|---|---|
|  | (Wgt %) | | | |
| Water | 50.00 | 50.00 | 50.00 | 50.00 |
| Ammonium Lauryl Sulfate | 10.00 | 10.00 | 8.00 | 6.00 |
| Ammonium Laureth Sulfate | 4.00 | 3.00 | 2.00 | 2.00 |
| Cocamide MEA | 2.00 | 2.00 | 2.00 | 2.00 |
| Ethylene Glycol Distearate | 2.00 | 2.00 | 2.00 | 2.00 |
| Cetyl Alcohol | 2.00 | 2.00 | 2.00 | 2.00 |
| Stearyl Alcohol | 1.20 | 1.20 | 1.20 | 1.20 |
| Glycerin | 1.00 | 1.00 | 1.00 | 1.00 |
| Polyquatemium 10 | 0.50 | 0.25 | 0.00 | 0.00 |
| Polyquatemium 24 | 0.00 | 0.00 | 0.50 | 0.25 |
| Ammonium Lauryl Sulfate | 1.50 | 1.50 | 1.50 | 1.50 |
| Sodium Chloride | 0.10 | 0.10 | 0.10 | 0.10 |
| Sucrose Polyesters of Cottonate Fatty Acid | 3.00 | 3.00 | 0.00 | 0.00 |
| Sucrose Polyesters of Behenate Fatty Acid | 2.00 | 3.00 | 0.00 | 0.00 |
| Polydimethyl Siloxane | 0.00 | 0.00 | 3.00 | 2.00 |
| Cocaminopropyl Betaine | 0.00 | 1.00 | 3.00 | 3.00 |
| Lauryl Dimethyl Amine Oxide | 1.50 | 1.50 | 1.50 | 1.50 |
| Decyl Polyglucose | 0.00 | 0.00 | 1.00 | 1.00 |
| DMDM Hydantoin | 0.15 | 0.15 | 0.15 | 0.15 |
| Modofied Polypeptides of Example 1–9 | 2.00 | 5.00 | 0.10 | 5.00 |
| Phenoxyethanol | 0.50 | 0.50 | 0.50 | 0.50 |
| Fragrance | 0.50 | 0.50 | 0.50 | 0.50 |
| Water | q.s. | q.s. | q.s. | q.s. |
|  | 100.00 | 100.00 | 100.00 | 100.00 |

Example 25

Liquid Dish Detergent

|  | (Wgt. %) |
|---|---|
| C12 Ethoxy (1) Sulfate | 12.00 |
| 2-methoxy Undecanoic Acid | 4.50 |
| C12 Ethoxy (2) Carboxylate | 4.50 |
| C12 Alcohol Ethoxylate (4) | 3.00 |
| C12 Amine Oxide | 3.00 |
| Sodium Cumene Sulfonate | 2.00 |
| Ethanol | 4.00 |
| Mg++ (as MgC12) | 0.20 |
| Ca++ (as CaC12) | 0.40 |
| Modified Polypeptide of Example 1–9 | 1.00 |
| Water | q.s. |
|  | 100.00 |

Examples 26–27

Laundry Detergent Powders

|  | Ex. 26 | Ex. 27 |
|---|---|---|
|  | (Wgt %) | |
| C13 Linear Alkylbenzene Sulfonate | 22.0 | 12.0 |
| Phosphate (as sodium tripolyphosphates) | 23.0 | 0.0 |
| Sodium Carbonate | 23.0 | 0.0 |
| Sodium Silicate | 14.0 | 0.0 |
| Zeolite | 8.2 | 26.0 |
| 2-butyl Octanoic Acid | 0.0 | 4.0 |
| Sodium C12–14 Secondary (2,3) Alkyl Sulfate | 0.0 | 5.0 |
| Sodium Citrate | 0.0 | 5.0 |
| Optical Brighter | 0.0 | 0.1 |

-continued

|  | Ex. 26 (Wgt %) | Ex. 27 |
|---|---|---|
| Diethyaenetriaminepentaacetic acid | 0.4 | 0.0 |
| Sodium Sulfate | 5.5 | 17.0 |
| Modified Polypeptide of Examples 1–9 | 3.0 | 0.2 |
| Water | q.s. | q.s. |
|  | 100.0 | 100.0 |

Example 28
Liquid Laundry Detergent

|  | (Wt. %) |
|---|---|
| $C_{13}$–$C_{17}$ Sodium Paraffin Sulfonate | 10.00 |
| Laureth-8 | 5.00 |
| Sodium Lauroamphodipropionate | 5.00 |
| Enzyme | 1.00 |
| Ethanol | 4.00 |
| Propylene Glycol | 6.00 |
| Polyquaternium-10 | 0.50 |
| Citric Acid | 2.00 |
| Triethanolamine | to pH 4.0 |
| Perfume | 1.00 |
| Modified Polypeptide of Examples 1–9 | 2.00 |
| Water | q.s. |
|  | 100.00 |

Examples 29–30
Hard Surface Cleaners

|  | Ex. 29 (Wt. %) | Ex. 30 |
|---|---|---|
| Sodium C12 Alkylbenzene Sulfonate | 1.95 | 0.00 |
| Sodium C12 Alkyl Sulfate | 0.00 | 2.20 |
| Sodium C12 Disthyleneglycol Monohexyl Ether Sulfate | 0.00 | 2.20 |
| C12 Dimethylamine Oxide | 0.00 | 0.50 |
| Sodium Cumene Sulfonate | 1.30 | 0.00 |
| Hexyl Carbitol | 6.30 | 6.30 |
| Modified Polypeptide of Examples 1–9 | 0.10 | 5.00 |
| Water | q.s. | q.s. |
|  | 100.00 | 100.00 |

Example 31
Dentifrice Composition

|  | (Wgt %) |
|---|---|
| Sorbitol (70% aqueous solution) | 35.0 |
| Polyethylene Glycol (MW = 600) | 1.0 |
| Silica dental abrasive | 20.0 |
| Sodium Flouride | 0.243 |
| Titanium Dioxide | 0.5 |
| Sodium Saccharin | 0.286 |
| Sodium Alkyl Sulfate (27.9% aqueous sol.) | 4.0 |
| Flavor | 1.0 |
| Carboxyvinyl Polymer | 0.3 |
| Carrageenan | 0.8 |
| Modified Polypeptide of Examples 1–9 | 5.0 |

-continued

|  | (Wgt %) |
|---|---|
| Water | q.s. |
|  | 100.0 |

Example 32
Mouthwash Composition

|  | (Wgt %) |
|---|---|
| SDA 40 Alcohol | 8.00 |
| Flavor | 0.08 |
| Sodium Fluoride | 0.05 |
| Glycerine | 10.00 |
| Sweetener | 0.02 |
| Benzoic acid | 0.05 |
| Sodium hydroxide | 0.20 |
| Modified Polypeptide of Examples 1–9 | 10.00 |
| Water | q.s. |
|  | 100.00 |

Example 33
Lozenge Composition

|  | (Wgt %) |
|---|---|
| Sorbitol | 17.50 |
| Mannitol | 17.50 |
| Starch | 13.60 |
| Sweetener | 1.20 |
| Flavor | 11.70 |
| Color | 0.10 |
| Modified Polypeptide of Examples 1–9 | 0.05 |
| Corn syrup | q.s. |
|  | 100.00 |

Example 34
Enzymatic Contact Lens Cleaning Solution

|  | (Wgt %) |
|---|---|
| Glucoes | 50.00 |
| Nonionic Surfactant (Polyoxyethylene-polyoxypropylene copolymer | 2.00 |
| Anionic Surfactant (Polyoxyethlene-alkylphenylether sodium sulfricester) | 1.00 |
| Sodium Chloride | 1.00 |
| Borax | 0.30 |
| Modified Polypeptide of Examples 1–9 | 1.00 |
| Water | q.s. |
|  | 100.00 |

What is claimed:

1. A modified polypeptide which has an enzymatic activity level of greater than about 70% of a parent polypeptide and an allergenic response level of less than about 33% of the parent polypeptide, wherein the parent polypeptide comprises an enzyme with no additional conjugation of polymer moieties.

2. A modified polypeptide according to claim 1 wherein the enzymatic activity level is greater than about 80% of a parent polypeptide and an allergenic response level of less than about 20% of the parent polypeptide.

3. A modified polypeptide with reduced allergenicity and high activity comprising the formula:

$$A\text{-}B_n$$

wherein:
a.) A is a proteolytic enzyme,
b.) B is a twin polymer moiety having a total molecular weight of from about 0.5 KD to about 40 KD, conjugated to the proteolytic enzyme, having the formula:

wherein $R_1$ and $R_2$ are essentially straight chain polymers, having a molecular weight ranging from about 0.25 KD to about 20 KD;
wherein the ratio of the molecular weights of $R_1$ and $R_2$ is from about 1:10 to about 10:1; and
wherein X is a linking moiety which links the twin polymer moiety to a single site on the enzyme; and
c.) n is from about 1 to about 15.

4. A modified polypeptide according to claim 3 wherein: the enzyme, A, is selected from the group consisting of lipase enzymes and protease enzymes, and mixtures thereof; and
the modified polypeptide has an enzymatic activity level of greater than about 70% of a parent polypeptide and an allergenic response level of less than about 33% of the parent polypeptide.

5. A modified polypeptide according to claim 4, wherein the enzyme, A, is selected from the group consisting of lipase enzymes and protease enzymes selected from the group consisting of subtilisin, chymotrypsin, and elastase enzymes, and mixtures thereof.

6. A modified polypeptide according to claim 5, wherein the enzyme is a subtilisin protease enzyme.

7. A modified polypeptide according to claim 6, wherein the enzyme is selected from the group consisting of bacterial serine protease enzyme, subtilisin BPN', Protease A, Protease B, Protease D, Protease F, and mixtures thereof.

8. A modified polypeptide according to claim 7, wherein the enzyme is Protease F.

9. A modified polypeptide according to claim 3 wherein the total molecular weight of the twin polymer moiety is from about 1 KD to about 10 KD and the individual polymer moieties, $R_1$ and $R_2$, have a molecular weight ranging from about 0.5 KD to about 5 KD.

10. A modified polypeptide according to claim 3 wherein the ratio of molecular weights of $R_1$ and $R_2$, is from about 1:5 to about 5:1.

11. A modified polypeptide according to claim 3 wherein the polymers, $R_1$ and $R_2$, comprise polyethylene glycol.

12. A modified polypeptide according to claim 3 wherein n is from about 1 to about 10.

13. A modified polypeptide with reduced allergenicity and high activity comprising the formula:

$$A\text{-}B_n$$

wherein
a.) A is Protease F;
b.) B is a twin polymer moiety, conjugated to the Protease F, having a total molecular weight of from about 1.0 KD to about 10 KD, each twin polymer moiety having the formula:

wherein $R_1$ and $R_2$ comprise essentially straight chain polyethylene glycol having a molecular weight of from about 0.5 KD to about 5 KD;
wherein the ratio of the molecular weights of $R_1$ and $R_2$ is from about 1:3 to about 3:1; and
wherein X is an activated lysine succinimidyl ester; and
c.) n is from about 1 to about 10.

14. A modified polypeptide according to claim 12, which exhibits enzymatic activity levels greater than 90% of the activity of Protease F and exhibits allergenic response levels of less than 5% of the allergenic response of Protease F.

15. A personal cleansing composition comprising greater than about 0.001% and less than about 20% of the modified polypeptide according to claim 3.

16. A laundry cleansing composition comprising greater than about 0.001% and less than about 20% of the modified polypeptide according to claim 3.

17. An oral cleansing composition comprising greater than about 0.001% and less than about 20% of the modified polypeptide according to claim 3.

18. A topical skin care composition comprising greater than about 0.001% and less than about 20% of the modified polypeptide according to claim 3.

19. A shower gel comprising greater than about 0.001% and less than about 10% of the modified polypeptide according to claim 3.

20. A leave-on skin moisturizer composition comprising greater than about 0.001% and less than about 10% of the modified polypeptide according to claim 3.

21. A cosmetic composition comprising greater than about 0.001% and less than about 10% of the modified polypeptide according to claim 3.

22. A cleansing wipe composition comprising a cleansing composition comprising greater than about 0.001% and less than about 10% of the modified polypeptide according to claim 3.

* * * * *